(12) United States Patent
Weisman et al.

(10) Patent No.: US 8,702,784 B2
(45) Date of Patent: Apr. 22, 2014

(54) OUTER TUBE FOR STENT REPOSITIONING AND DEPLOYMENT

(75) Inventors: Michal Weisman, Palo Alto, CA (US); Eric Schneider, Lincoln, RI (US); Gary J. Leanna, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 138 days.

(21) Appl. No.: 13/272,945

(22) Filed: Oct. 13, 2011

(65) Prior Publication Data

US 2012/0095567 A1  Apr. 19, 2012

Related U.S. Application Data

(60) Provisional application No. 61/393,101, filed on Oct. 14, 2010.

(51) Int. Cl.
  *A61F 2/06*  (2013.01)
  *A61F 2/02*  (2006.01)
  *A61M 25/00*  (2006.01)

(52) U.S. Cl.
  USPC ............ 623/1.11; 623/1.23; 623/23.7; 604/8; 604/264

(58) Field of Classification Search
  USPC ................ 623/1.11, 1.12, 23.64–23.66, 23.7; 604/8, 263, 264, 280, 500, 514, 523, 604/540, 544
  See application file for complete search history.

(56) References Cited

U.S. PATENT DOCUMENTS

| | | |
|---|---|---|
| 4,382,445 A | 5/1983 | Sommers |
| 4,592,341 A | 6/1986 | Omagari et al. |
| 4,699,611 A | 10/1987 | Bowden |
| 4,931,037 A | 6/1990 | Wetterman |
| 4,950,228 A | 8/1990 | Knapp, Jr. et al. |
| 4,955,858 A | 9/1990 | Drews |
| 4,957,479 A | 9/1990 | Roemer |
| 4,973,301 A | 11/1990 | Nissenkorn |
| 4,990,133 A | 2/1991 | Solazzo |
| 5,052,998 A | 10/1991 | Zimmon |
| 5,152,749 A | 10/1992 | Giesy et al. |
| 5,160,341 A | 11/1992 | Brenneman et al. |
| 5,334,185 A | 8/1994 | Giesy et al. |
| 5,372,600 A | 12/1994 | Beyar et al. |

(Continued)

FOREIGN PATENT DOCUMENTS

| | | |
|---|---|---|
| EP | 1 872 749 | 1/2008 |
| WO | 02/03889 | 1/2002 |
| WO | 2011/046726 | 4/2011 |

*Primary Examiner* — David Isabella
*Assistant Examiner* — Yashita Sharma
(74) *Attorney, Agent, or Firm* — Seager, Tufte & Wickhem, LLC

(57) ABSTRACT

A drainage stent delivery system including a stent, a guide catheter, a push catheter, and an outer sheath. The guide catheter extends through the lumen of the stent and the push catheter is disposed over a portion of the guide catheter proximal of the distal end of the stent. The outer sheath is slidably disposed over the push catheter and surrounding at least a portion of the stent. The outer sheath may be actuated from a first position in which a distal portion of the outer sheath surrounds the stent to a second position in which the distal portion of the outer sheath is proximal of the stent. The stent delivery system may also include a retention mechanism for selectively coupling the stent to the outer sheath which may selectively decouple the stent from the outer sheath through rotational and/or translational motion of the outer sheath relative to the stent.

10 Claims, 15 Drawing Sheets

(56) References Cited

U.S. PATENT DOCUMENTS

| | | |
|---|---|---|
| 5,401,257 A | 3/1995 | Chevalier, Jr. et al. |
| 5,507,464 A | 4/1996 | Hamerski et al. |
| 5,599,291 A | 2/1997 | Balbierz et al. |
| 5,681,274 A | 10/1997 | Perkins et al. |
| 5,690,643 A | 11/1997 | Wijay |
| 5,921,952 A | 7/1999 | Desmond, III et al. |
| 5,921,971 A | 7/1999 | Agro et al. |
| 6,245,076 B1 | 6/2001 | Yan |
| 6,248,100 B1 | 6/2001 | de Toledo et al. |
| 6,264,624 B1 | 7/2001 | Desmond, III et al. |
| 6,562,024 B2 | 5/2003 | Alvarez de Toledo et al. |
| 6,620,191 B1 | 9/2003 | Svensson |
| 7,198,637 B2 | 4/2007 | Deshmukh et al. |
| 7,763,008 B2 | 7/2010 | Yu |
| 7,879,080 B2 | 2/2011 | Sato |
| 2003/0047654 A1 | 3/2003 | Johansson et al. |
| 2005/0085891 A1 | 4/2005 | Goto et al. |
| 2005/0085892 A1 | 4/2005 | Goto et al. |
| 2006/0068144 A1 | 3/2006 | Mizuno et al. |
| 2006/0276873 A1 | 12/2006 | Sato |
| 2007/0293929 A1 | 12/2007 | Aoba et al. |
| 2008/0004685 A1 | 1/2008 | Seemann et al. |
| 2009/0143849 A1 | 6/2009 | Ozawa et al. |
| 2009/0312829 A1 | 12/2009 | Aoba et al. |
| 2011/0077622 A1 | 3/2011 | Weisman et al. |
| 2011/0295265 A1 | 12/2011 | Hollett et al. |
| 2011/0313404 A1 | 12/2011 | Amos et al. |
| 2011/0319904 A1 | 12/2011 | Hollett et al. |

US 8,702,784 B2

OUTER TUBE FOR STENT REPOSITIONING AND DEPLOYMENT

RELATED APPLICATIONS

This application claims the benefit U.S. Provisional Application No. 61/393,101, filed Oct. 14, 2010, the disclosure of which is incorporated herein in its entirety.

TECHNICAL FIELD

The disclosure is directed to a retention structure of a medical device. More particularly, the disclosure is directed to a stent retention structure for selectively retaining a stent to a shaft of a stent delivery system. Specifically, the disclosure is directed to a retention structure for selectively securing a drainage stent to a catheter shaft of a drainage stent delivery system.

BACKGROUND

Medical devices, such as catheters, are widely used in various medical procedures to access remote anatomical locations and/or deploy therapeutic devices. One exemplary catheter system is a drainage stent delivery system configured to deliver a drainage stent (e.g., a drainage catheter) to a body lumen, such as a lumen of the biliary tree or a ureter. It may be desirable to releasably connect the drainage stent to the delivery system in order to provide the medical personnel with control over positioning and deployment of the drainage catheter in a body lumen without premature deployment of the drainage stent from the delivery system. Some exemplary drainage stent delivery systems including features for releasably connecting a drainage stent to a delivery system are disclosed in U.S. Pat. Nos. 5,921,952 and 6,562,024, the disclosures of which are incorporated herein by reference. For instance, a releasable connecting feature in the form of a flexible thread or suture may be used for releasably connecting the drainage stent to a shaft of the drainage stent delivery system.

However, a need remains to provide alternative embodiments of a retention system to releasably couple a stent, such as a vascular stent or a drainage stent, or other endoprosthesis to a stent delivery system, such as a vascular stent or drainage stent delivery system, which allows controlled positioning and deployment of the stent in a body lumen.

SUMMARY

The disclosure is directed to several alternative designs and configurations of medical device structures and assemblies including a retention structure for selectively securing a stent to a delivery system.

Accordingly, one illustrative embodiment is a stent delivery system including a stent, a guide catheter, a push catheter, and an outer sheath. The stent has a proximal end, a distal end, and a lumen extending therethrough. The guide catheter extends through the lumen of the stent and the push catheter is disposed over a portion of the guide catheter proximal of the distal end of the stent. The outer sheath is slidably disposed over the push catheter and surrounding at least a portion of the stent. The outer sheath is actuatable from a first position in which a distal portion of the outer sheath surrounds at least a portion of the stent to a second position in which the distal portion of the outer sheath is proximal of the proximal end of the stent. The stent delivery system also includes a retention mechanism for selectively coupling the stent to the outer sheath through rotational motion of the outer sheath relative to the stent.

Another illustrative embodiment is a drainage stent delivery system including a drainage stent, a guide catheter, a push catheter, and an outer sheath. The drainage stent includes a tubular member having a proximal end, a distal end and a lumen extending therethrough. The guide catheter extends from a handle assembly to a location distal of the distal end of the drainage stent. The push catheter has a distal end proximate the proximal end of the drainage stent and extends proximally around the guide catheter to the handle assembly. The outer sheath is slidably disposed over the push catheter. The outer sheath is actuatable from a first position in which a distal portion of the outer sheath is engaged with the drainage stent to a second position in which the distal portion of the outer sheath is disengaged from the drainage stent. In a first rotational orientation the outer sheath is not actuatable from the first position to the second position and in a second rotational orientation the outer sheath is actuatable from the first position to the second position.

Yet another illustrative embodiment is a method of selectively releasing a stent from a stent delivery system. The method includes providing a stent disposed over a distal portion of a guide catheter and positioned distal of a push catheter surrounding the guide catheter. An outer sheath is provided having a distal portion slidably disposed over a proximal portion of the stent. The outer sheath is actuated from a first position in which the distal portion of the outer sheath is engaged with the stent to a second position in which the distal portion of the outer sheath is disengaged from the stent. Actuating the outer sheath from the first position to the second position requires rotating the distal portion of the outer sheath relative to the stent to permit actuation of the outer sheath from the first position to the second position.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
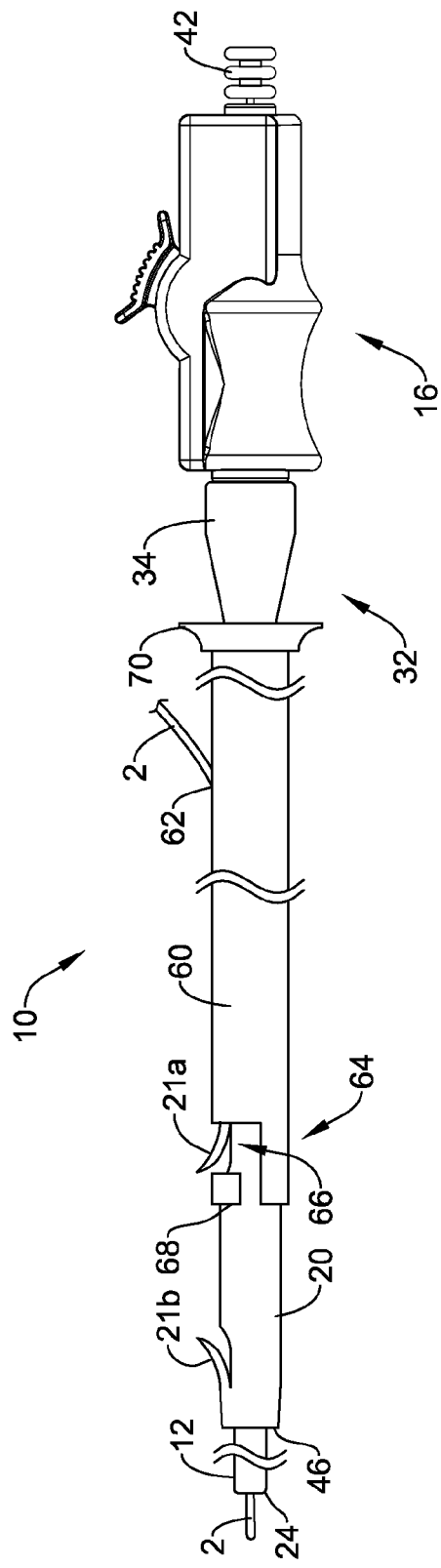
FIG. 1 is a plan view of an exemplary drainage stent delivery system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "proximal" refers to a direction that is generally toward a physician during a medical procedure, while the term "distal" refers to a direction that is generally toward a target site within a patient's anatomy during a medical procedure.

As used in this specification and the appended claims, the term "body lumen" means any body passage cavity that conducts fluid, including but not limited to biliary ducts, pancreatic ducts, ureteral passages, esophagus, and blood vessels such as those of the human vasculature system.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
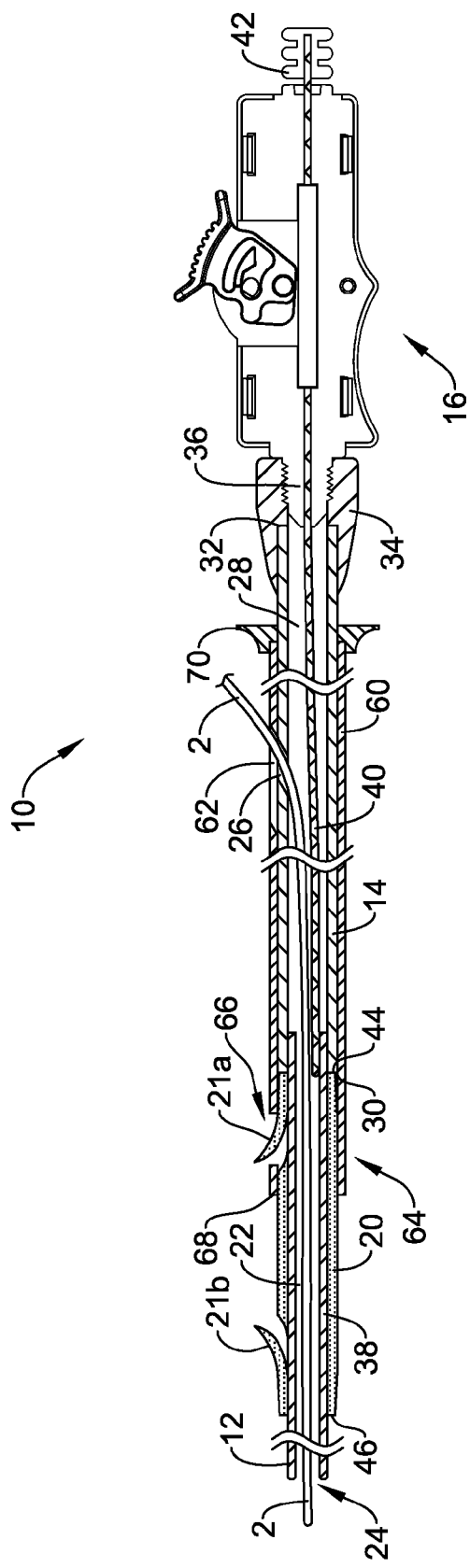
FIG. 2 is a longitudinal cross-sectional view of the drainage stent delivery system of FIG. 1.

Referring now to FIGS. 1 and 2, there is shown an exemplary medical device, illustrated as a drainage stent delivery system 10 for delivering a drainage catheter or stent 20 to an anatomical location, such as in a lumen of the biliary tree or a ureter. The drainage stent 20 may be used to bypass or drain an obstructed lumen and can be configured for long-term positioning within the lumen. The drainage stent 20 may be an elongate tubular member which is generally not expandable. The drainage stent 20 may have a proximal end 44, a distal end 46 and a lumen extending through the drainage stent 20 from the proximal end 44 to the distal end 46. In some embodiments, the drainage stent 20 may include one or more, or a plurality of barbs 21, or other retention features that may help prevent migration of the drainage stent 20 when positioned in a body lumen. The illustrated drainage stent 20 includes a proximal barb 21a and a distal barb 21b. It should be understood that the terms "drainage catheter" and "drainage stent" can be used interchangeably with reference to these applications.

The drainage stent delivery system 10 is designed for use with a conventional guidewire 2 and may include a drainage stent 20, a guide catheter 12, a push catheter 14, an outer sheath 60 and a handle assembly 16. The guidewire 2 may extend into a lumen 22 of the guide catheter 12 through a distal guidewire port 24 and out a proximal guidewire port 26 in a sidewall of the push catheter 14 and a proximal guidewire port 62 in a sidewall of the outer sheath 60, providing the drainage stent delivery system 10 with single-operator-exchange (SOE) capabilities. In some instances, the proximal guidewire port 62 of the outer sheath 60 may be an elongate slit or slot allowing for longitudinal movement of the outer sheath 60 while the guidewire 2 is positioned through the proximal guidewire port 62.

The guide catheter 12 may be slidably disposed in the lumen 28 of the push catheter 14 and extend distally from the distal end 30 of the push catheter 14. The guide catheter 12 may extend through the drainage stent 20 to a location distal of the drainage stent 20. In some embodiments, a distal portion of the push catheter 14, or a component thereof, may extend into the lumen of the drainage stent 20. In some instances, the proximal end of the drainage stent 20 may abut and/or face a distal end or rim 30 of the push catheter 14, or a component thereof, while a distal portion or component of the push catheter 14 extends into the lumen of the drainage stent 20. In other embodiments, the push catheter 14, or a component thereof, may extend over the drainage stent 20, surrounding a portion of the drainage stent 20.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, or other suitable means. In some instances, a component of the push catheter 14 may be longitudinally (e.g., slidably and/or rotatably) actuatable relative to another component of the push catheter 14. In such embodiments, the handle assembly 16 may be configured such that the actuatable component of the push catheter 14 may be actuated by medical personnel while the stationary component of the push catheter 14 remains stationary relative to the handle assembly 16.

The guide catheter 12 may include a distal tubular portion 38 and a proximal elongate wire 40, such as a pull wire, coupled to the distal tubular portion 38. The elongate wire 40 may be coupled to the distal tubular portion 38 at a coupling location. The elongate wire 40 may extend through the lumen 28 of the push catheter 14 to the handle assembly 16 while the distal tubular portion 38 extends through the drainage stent 20 to a location distal of the drainage stent 20. In some embodiments, the elongate wire 40 may extend through the handle assembly 16 to a location proximal of the handle assembly 16. The proximal end of the elongate wire 40 may terminate at a knob 42 which may be grasped by an operator to manipulate the guide catheter 12. Actuation of the knob 42 thus may longitudinally actuate the guide catheter 12 relative to the push catheter 14.

As shown in FIG. 2, the elongate wire 40 may share the lumen 28 of the push catheter 14 with the guidewire 2 along a portion of the length of the elongate wire 40. Thus, a portion of the elongate wire 40 may extend proximally from the tubular portion 38 along the side of the guidewire 2 through the lumen 28 of the push catheter 14 up to a location where the guidewire 2 exits the proximal guidewire port 26 of the push catheter 14.

The outer sheath 60 may be slidably disposed over and surrounding the push catheter 14. The outer sheath 60 may include an actuator 70, such as a collar, lever, handle, knob, or other actuation mechanism, proximate the proximal end of the outer sheath 60 to be manipulated by a user to actuate the outer sheath 60. A user may use the actuator 70 to effect longitudinal and/or rotational movement of the outer sheath 60.

The outer sheath 60 may include a distal portion 64 sized to be positioned over and surround at least a proximal portion of the drainage stent 20, such that the distal end 68 of the outer sheath 60 is located distal of the proximal end 44 of the drainage stent 20. In some embodiments, the distal portion 64 of the outer sheath 60 may extend over the entire length, substantially the entire length, or only a proximal portion of the drainage stent 20.

The outer sheath 60 may provide a means for releasably connecting the drainage stent 20 to the drainage stent delivery system 10. When the drainage stent 20 has been properly placed, the drainage stent 20 may be disconnected from the drainage stent delivery system 10 such that the drainage stent 20 remains in the lumen as the guide catheter 12, the push catheter 14 and/or the outer sheath 60 are withdrawn. Some exemplary retention mechanisms for selectively coupling the drainage stent 20 to the outer sheath 60 or other component of the drainage stent delivery system 10 are further described herein.

During a medical procedure, the drainage stent delivery system 10 may be advanced to a target location in the anatomy of a patient. For instance, the drainage stent delivery system 10 may be advanced over the guidewire 2 to a target location. In some instances, the drainage stent delivery system 10 may be tracked over the guidewire 2 as the drainage stent delivery system 10 is advanced through a working channel of an endoscope. The guidewire 2 may pass through the lumen 22 of the guide catheter 12 and the lumen 28 of the push catheter 14 and exit through the proximal guidewire port 26 of the push catheter 14.

When the drainage stent 20 has been positioned at the target location in a lumen, the operator may then selectively disengage the drainage stent 20 from the drainage stent delivery system 10 and withdraw the drainage stent delivery system 10, or components thereof, proximally relative to the drainage stent 20 to deploy the drainage stent 20 at the target location. For instance, in some embodiments actuation of the outer sheath 60 of the drainage stent delivery system 10 relative to the drainage stent 20 may disengage or unlock the drainage stent 20 from the outer sheath 60 of the drainage stent delivery system 10. In some instances, the outer sheath 60 must be rotated relative to the drainage stent 20 to permit longitudinal translation of the outer sheath 60 over the push catheter 14. Once the drainage stent 20 is disengaged from the outer sheath 60, withdrawing the guide catheter 12 proximally while the proximal end 44 of the drainage stent 20 abuts the distal end 30 of the push catheter 14, holding the drainage stent 20 stationary relative to the push catheter 14, may release the drainage stent 20 from the drainage stent delivery system 10 in order to deploy the drainage stent 20 at the target location. Once the drainage stent 20 has been properly deployed at the target location, the drainage stent delivery system 10 may then be withdrawn.

Some exemplary retention structures for selectively coupling the drainage stent 20 to the outer sheath 60 of the drainage stent delivery system 10 will now be further described. The retention structures may be used to selectively deploy, reposition and/or retrieve the drainage stent 20 during a medical procedure.

FIGS. 3A-3D illustrate the functionality of a first exemplary retention structure for selectively coupling the drainage stent 20 to the outer sheath 60 of the drainage stent delivery system 10. Although the drainage stent 20 is illustrated as being selectively coupled to the outer sheath 60 of the drainage stent delivery system 10, it is understood that in some embodiments the drainage stent 20 may be selectively coupled to another elongate shaft of the drainage stent delivery system 10, in the manner described with regard to FIGS. 3A-3D.

Figure 3A:
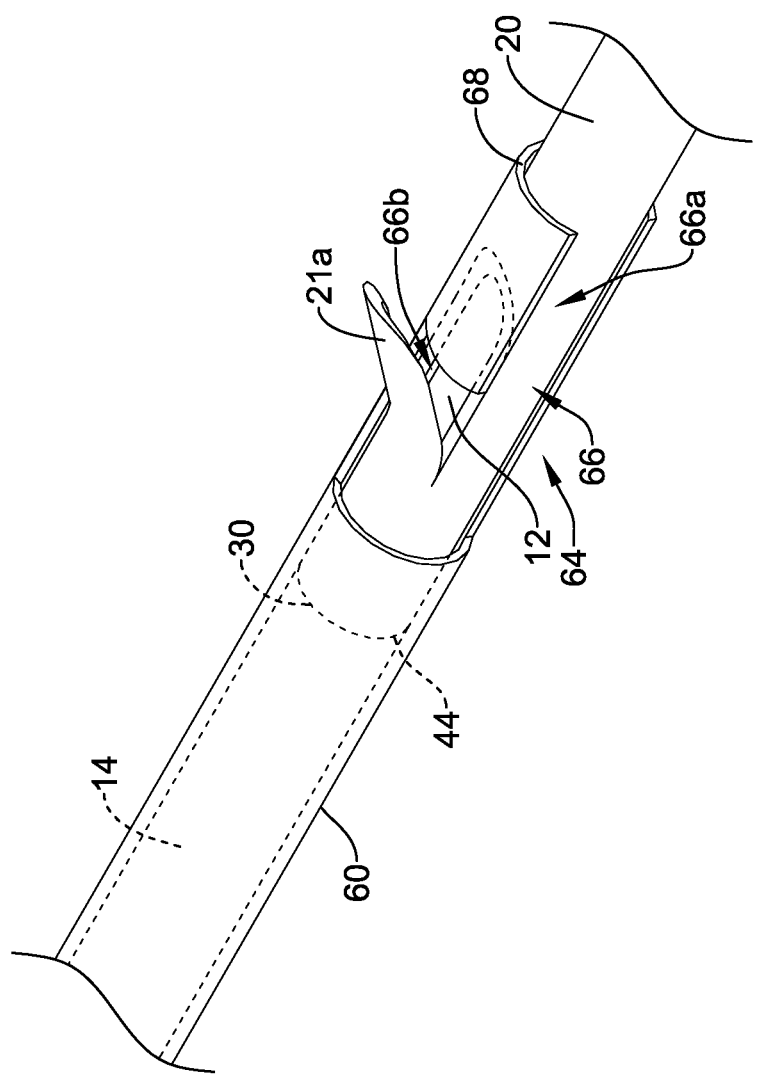
FIGS. 3A-3D are perspective views illustrating the functionality of an exemplary retention structure for selectively retaining a stent to an elongate shaft of a delivery system.

As shown in FIG. 3A, the outer sheath 60 may include an engaging feature which engages with a portion of the drainage stent 20 to selectively couple the drainage stent 20 to the outer sheath 60. For instance, the distal portion 64 of the outer sheath 60 may include an opening, such as the slot 66, configured to receive a portion of the drainage stent 20. The slot 66 may be formed in or through the tubular wall of the outer sheath 60. As shown in FIGS. 3A-3D, in some instances, the slot 66 may be an L-shaped slot, opening out to the distal end 68 of the outer sheath 60. The slot 66 may extend through the entire thickness of the tubular wall of the outer sheath 60, or the slot 66 may only extend through a portion of the thickness of the tubular wall of the outer sheath 60 (e.g., a groove). The slot 66, shown as an L-shaped slot, may include a first portion 66a extending generally longitudinally from the distal end 68 of the outer sheath 60 and a second portion 66b extending circumferentially from the first portion 66a in a direction deviating from the first portion 66a, leaving a portion of the tubular wall of the outer sheath 60 between the second portion 66b and the distal end 68 of the outer sheath 60.

A proximal portion of the drainage stent 20 may extend into the distal portion 64 of the outer sheath such that the distal portion 64 of the outer sheath 60 surrounds at least a portion of the drainage stent 20. It is noted that the distal portion 64 of the outer sheath 60 may extend over the drainage stent 20 for any desired length such that the proximal end 44 of the drainage stent 20 is positioned proximal of the distal end 68 of the outer sheath 60. When disposed in the distal portion 64 of the outer sheath 60, the proximal end 44 of the drainage stent 20 may face and/or abut the distal end 30 of the push catheter 14, which extends through the lumen of the outer sheath 60, while the guide catheter 12 extends through the lumen 28 of the push catheter 14 and the lumen of the drainage stent 20.

An engagement feature of the drainage stent 20 may extend into the slot 66 of the distal portion 64 of the outer sheath 60 to selectively couple the drainage stent 20 to the outer sheath 60. For instance, the proximal barb 21a of the drainage stent 20 may project outward from the tubular wall of the drainage stent 20 through the slot 66 of the outer sheath 60. Actuation (e.g., rotation and/or translation) of the outer sheath 60 may move the barb 21a into and out of the slot 66 to selectively couple and uncouple the drainage stent 20.

FIG. 3A illustrates the outer sheath 60 in a first or engaged position in which the drainage stent 20 is coupled to the distal portion 64 of the outer sheath 60. In the engaged position, the barb 21a may be positioned in the second portion 66b of the slot 66 such that longitudinal movement of the outer sheath 60 relative to the drainage stent 20 will not decouple or disengage the drainage stent 20 from the outer sheath 60. For instance, a portion of the tubular wall of the outer sheath 60 may be located distal of the barb 21a such that if the drainage stent 20 is moved distally relative to the outer sheath 60, the barb 21a will contact the tubular wall of the outer sheath 60 distal of the second portion 66b of the slot 66, preventing disengagement of the drainage stent 20.

Figure 3B:
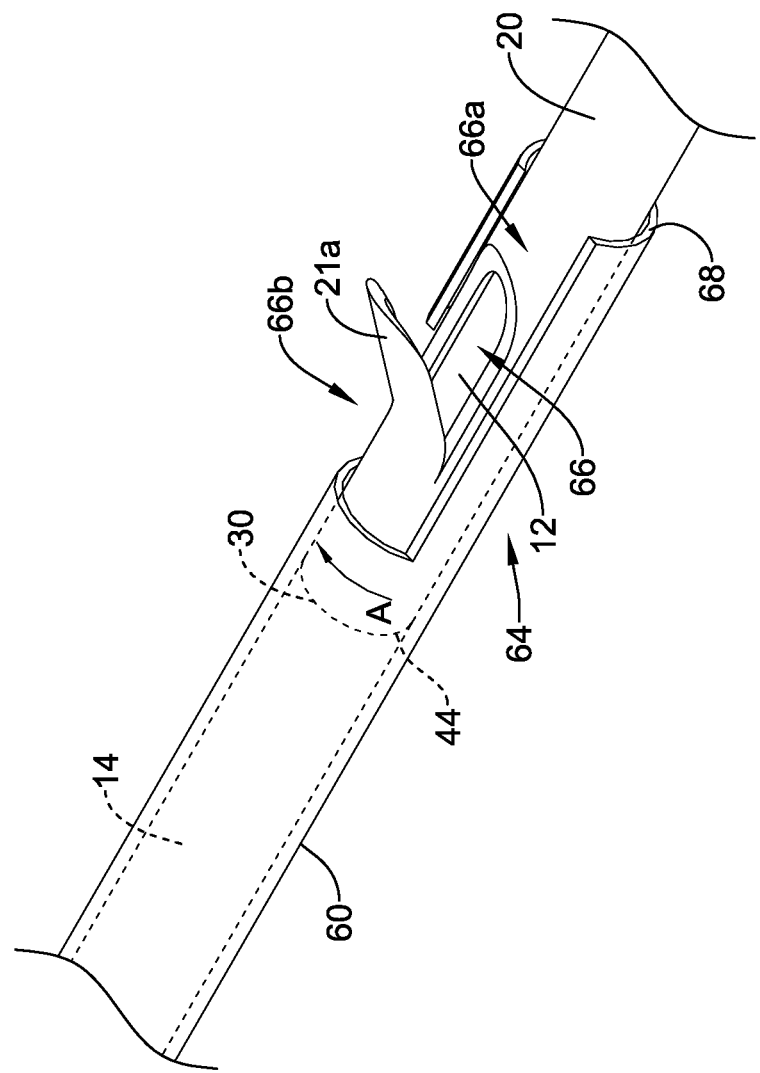
Figure 3C:
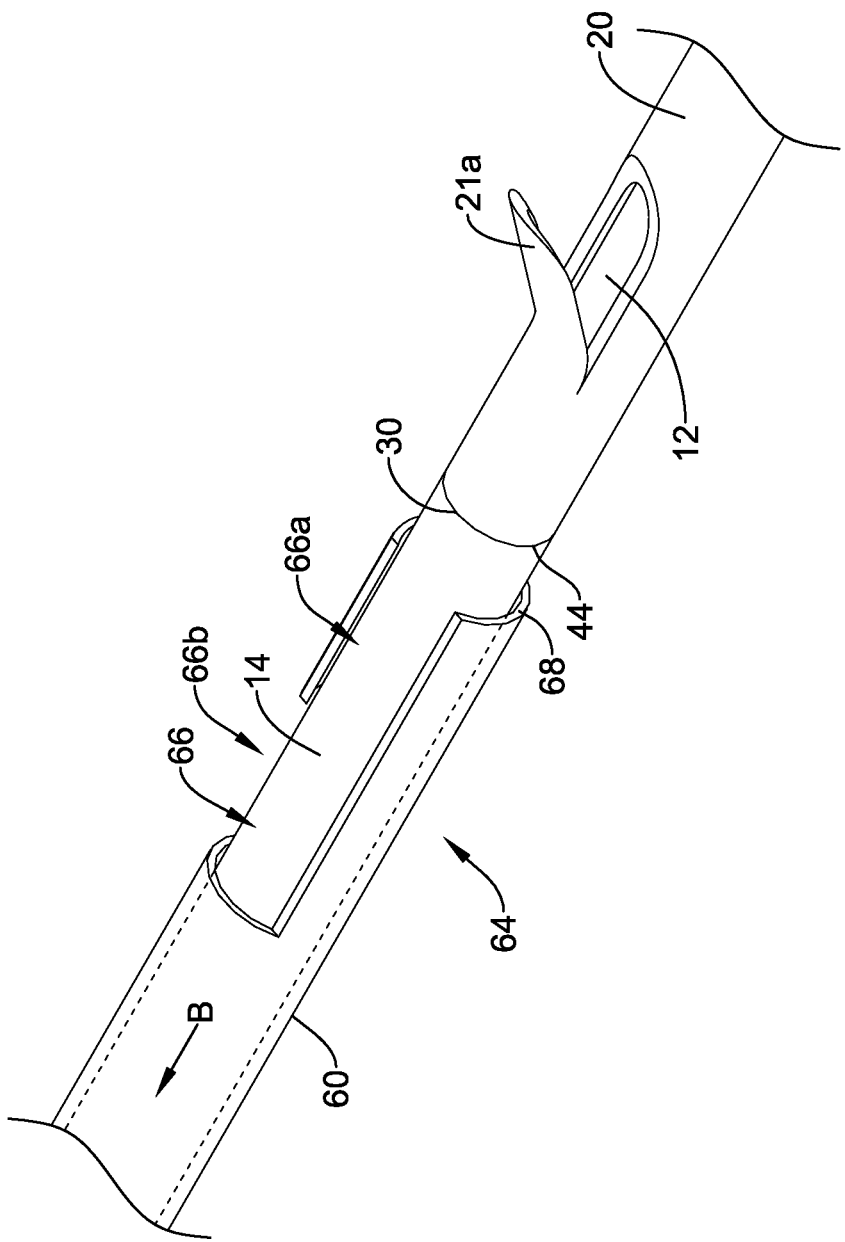

As shown in FIG. 3B at arrow A, in order to decouple the drainage stent 20 from the drainage stent delivery system 10, the outer sheath 60 may be rotated relative to the drainage stent 20 to move the barb 21a along the second portion 66b to a location that intersects the first portion 66a of the slot 66 in the distal portion 64 of the outer sheath 60. Once the barb 21a is located at the intersection of the first portion 66a and the second portion 66b of the slot 66, the outer sheath 60 may be translated longitudinally relative to the drainage stent 20 in a proximal direction, shown by arrow B of FIG. 3C, to a second or disengaged position to withdraw the barb 21a from the slot 66. Thus, subsequent to rotating the distal portion 64 of the outer sheath 60, the outer sheath 60 may be withdrawn proximally (e.g., translated longitudinally) to a second position such that the distal end 68 of the outer sheath 60 is proximal of the proximal end 44 of the drainage stent 20. Accordingly, in a first rotational orientation, shown in FIG. 3A, the barb 21a is not releasable from the slot 66 through longitudinal actuation of the outer sheath 60, and in a second rotational orientation, shown in FIG. 3B, the barb 21a is releasable from the slot 66 through longitudinal actuation of the outer sheath 60. Moreover, in the first rotational orientation, the outer sheath 60 is not longitudinally actuatable or translatable from the first position to the second position, but in the second rotational orientation, the outer sheath 60 is longitudinally actuatable or translatable from the first position to the second position. Thus, in at least some instances actuating the outer sheath 60 from the first position to the second position requires rotating the distal portion 64 of the outer sheath 60 relative to the drainage stent 20 to permit longitudinal actuation or translation of the outer sheath 60 from the first position to the second position.

Figure 3D:
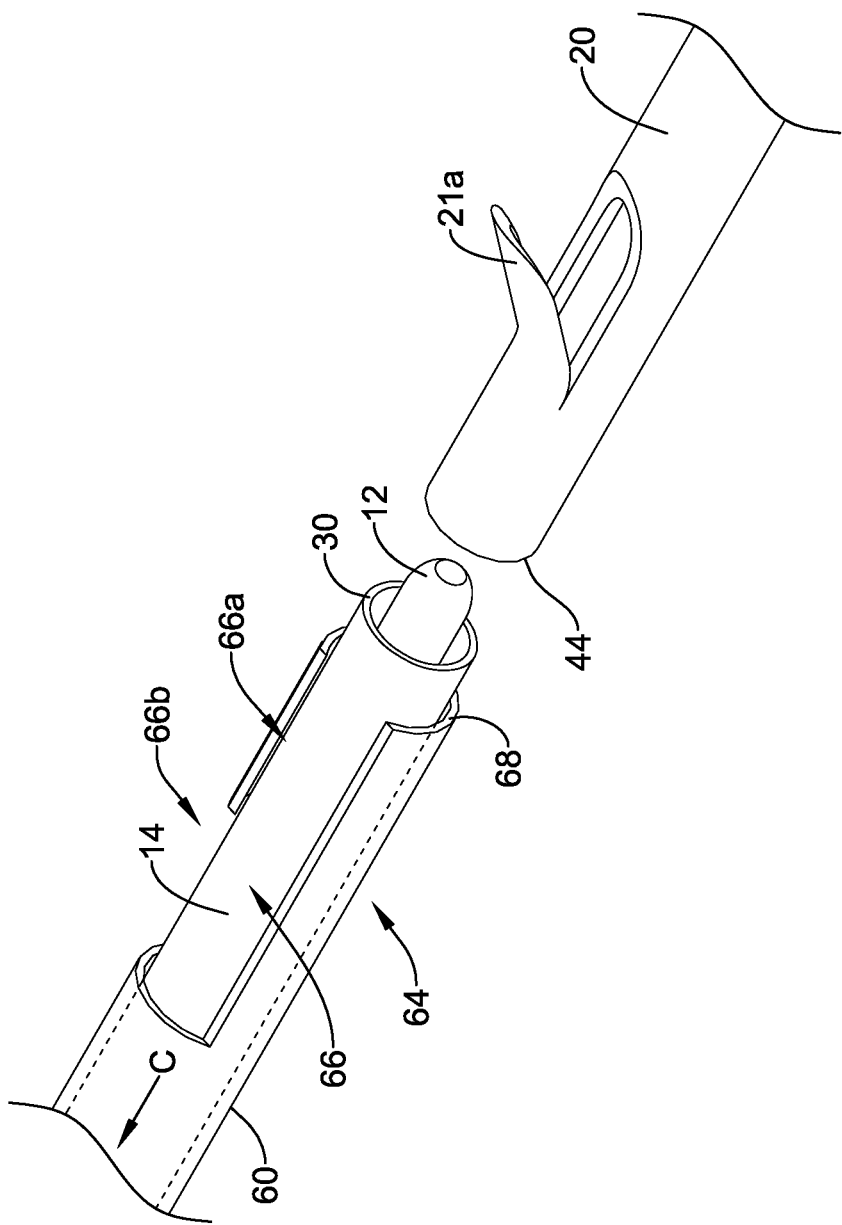

As shown by arrow C in FIG. 3D, with the barb 21a removed from the slot 66, the push catheter 14 and guide catheter 12, along with the outer sheath 60, may be withdrawn proximally while the drainage stent 20 is maintained at the target location in a body lumen. The push catheter 14, guide catheter 12 and the outer sheath 60 may be withdrawn proximally in any desired order. For example, in some instances, the guide catheter 12 may be withdrawn first, leaving the push catheter 14 in position with the distal end 30 of the push catheter facing and/or abutting the proximal end 44 of the drainage stent 20 to hold the drainage stent 20 stationary while the guide catheter 12 is withdrawn from the lumen of the drainage stent 20. Subsequently, the push catheter 14, the guide catheter 12, and the outer sheath 60, may be withdrawn from the patient. In other instances, the push catheter 14, the guide catheter 12, and/or the outer sheath 60, may be withdrawn simultaneously or sequentially in another desired order.

In instances in which it is desired to reposition and/or retrieve the drainage stent 20, the process of decoupling the outer sheath 60 from the drainage stent 20 may be reversed. For example, the outer sheath 60 may be advanced distally such that the proximal barb 21a passes into the first portion 66a of the slot 66. The outer sheath 60 may then be rotated relative to the drainage stent 20 to position the proximal barb 21a in the second portion 66b of the slot 66 to couple the drainage stent 20 to the outer sheath 60. With the drainage stent 20 coupled to the outer sheath 60, the outer sheath 60 may be actuated (advanced/withdrawn) to reposition and/or retrieve the drainage stent 20.

FIGS. 4A-4D illustrate the functionality of another exemplary retention structure for selectively coupling the drainage stent 20 to the outer sheath 60 of the drainage stent delivery system 10. Although the drainage stent 20 is illustrated as being selectively coupled to the outer sheath 60 of the drainage stent delivery system 10, it is understood that in some embodiments the drainage stent 20 may be selectively coupled to another elongate shaft of the drainage stent delivery system 10, in the manner described with regard to FIGS. 4A-4D.

Figure 4A:
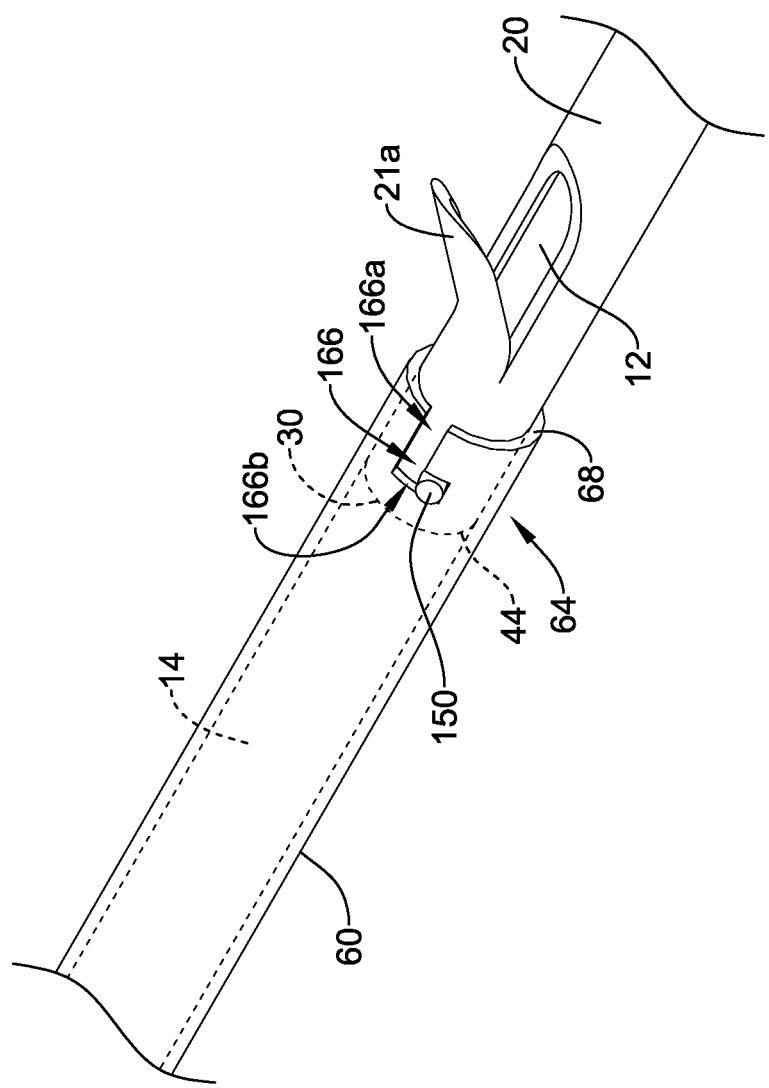
FIGS. 4A-4D are perspective views illustrating the functionality of another retention structure for selectively retaining a stent to an elongate shaft of a delivery system.

As shown in FIG. 4A, the outer sheath 60 may include an engaging feature which engages with a portion of the drainage stent 20 to selectively couple the drainage stent 20 to the outer sheath 60. For instance, the distal portion 64 of the outer sheath 60 may include an opening, such as the slot 166, configured to receive a portion of the drainage stent 20. The slot 166 may be formed in or through the tubular wall of the outer sheath 60. As shown in FIGS. 4A-4D, in some instances, the slot 166 may be an L-shaped slot, opening out to the distal end 68 of the outer sheath 60. The slot 166 may extend through the entire thickness of the tubular wall of the outer sheath 60, or the slot 166 may only extend through a portion of the thickness of the tubular wall of the outer sheath 60 (e.g., a groove). The slot 166, shown as an L-shaped slot, may include a first portion 166a extending generally longitudinally from the distal end 68 of the outer sheath 60 and a second portion 166b extending circumferentially from the first portion 166a in a direction deviating from the first portion 166a, leaving a portion of the tubular wall of the outer sheath 60 between the second portion 166b and the distal end 68 of the outer sheath 60.

A proximal portion of the drainage stent 20 may extend into the distal portion 64 of the outer sheath such that the distal portion 64 of the outer sheath 60 surrounds at least a portion of the drainage stent 20. It is noted that the distal portion 64 of the outer sheath 60 may extend over the drainage stent 20 for any desired length such that the proximal end 44 of the drainage stent 20 is positioned proximal of the distal end 68 of the outer sheath 60. When disposed in the distal portion 64 of the outer sheath 60, the proximal end 44 of the drainage stent 20 may face and/or abut the distal end 30 of the push catheter 14, which extends through the lumen of the outer sheath 60, while the guide catheter 12 extends through the lumen 28 of the push catheter 14 and the lumen of the drainage stent 20.

An engagement feature of the drainage stent 20 may extend into the slot 166 of the distal portion 64 of the outer sheath 60 to selectively couple the drainage stent 20 to the outer sheath 60. For instance, the drainage stent 20 may include a radially extending protrusion 150 projecting outward from the tubular wall of the drainage stent 20 through the slot 166 of the outer sheath 60. Actuation (e.g., rotation and/or translation) of the outer sheath 60 may move the protrusion 150 into and out of the slot 166 to selectively couple and uncouple the drainage stent 20.

FIG. 4A illustrates the outer sheath 60 in a first or engaged position in which the drainage stent 20 is coupled to the distal portion 64 of the outer sheath 60. In the engaged position, the protrusion 150 may be positioned in the second portion 166b of the slot 166 such that longitudinal movement of the outer sheath 60 relative to the drainage stent 20 will not decouple or disengage the drainage stent 20 from the outer sheath 60. For instance, a portion of the tubular wall of the outer sheath 60 may be located distal of the protrusion 150 such that if the drainage stent 20 is moved distally relative to the outer sheath 60, the protrusion 150 will contact the tubular wall of the outer sheath 60 distal of the second portion 166b of the slot 166, preventing disengagement of the drainage stent 20.

Figure 4B:
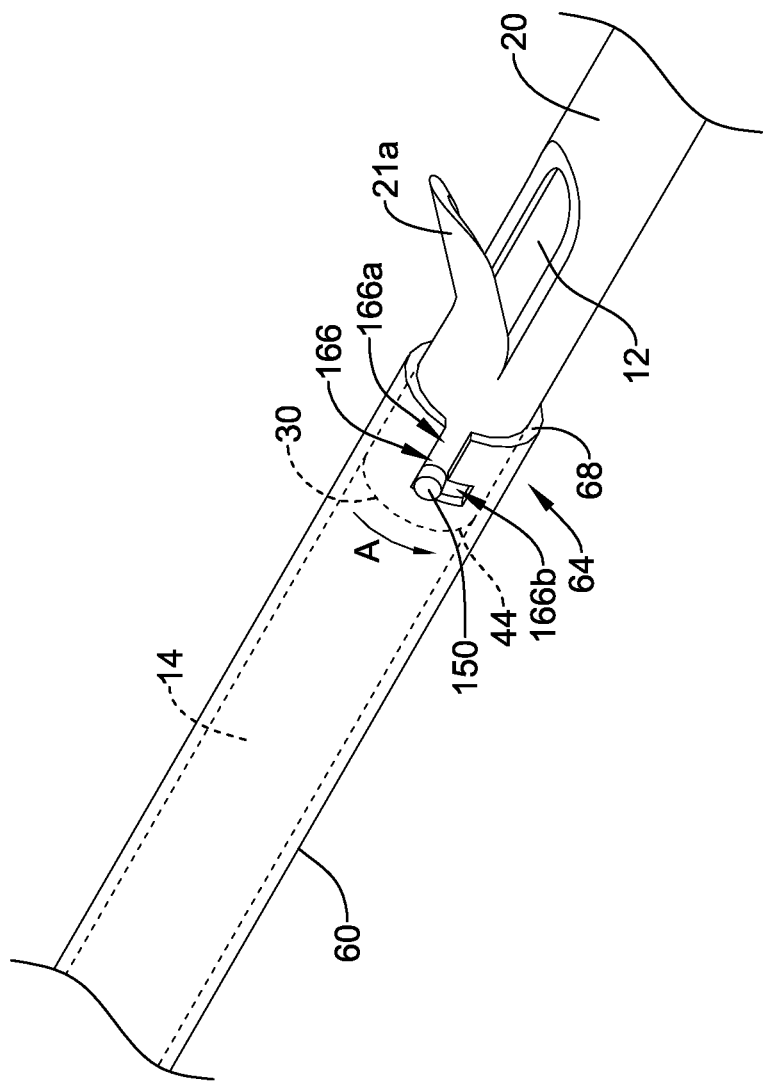
Figure 4C:
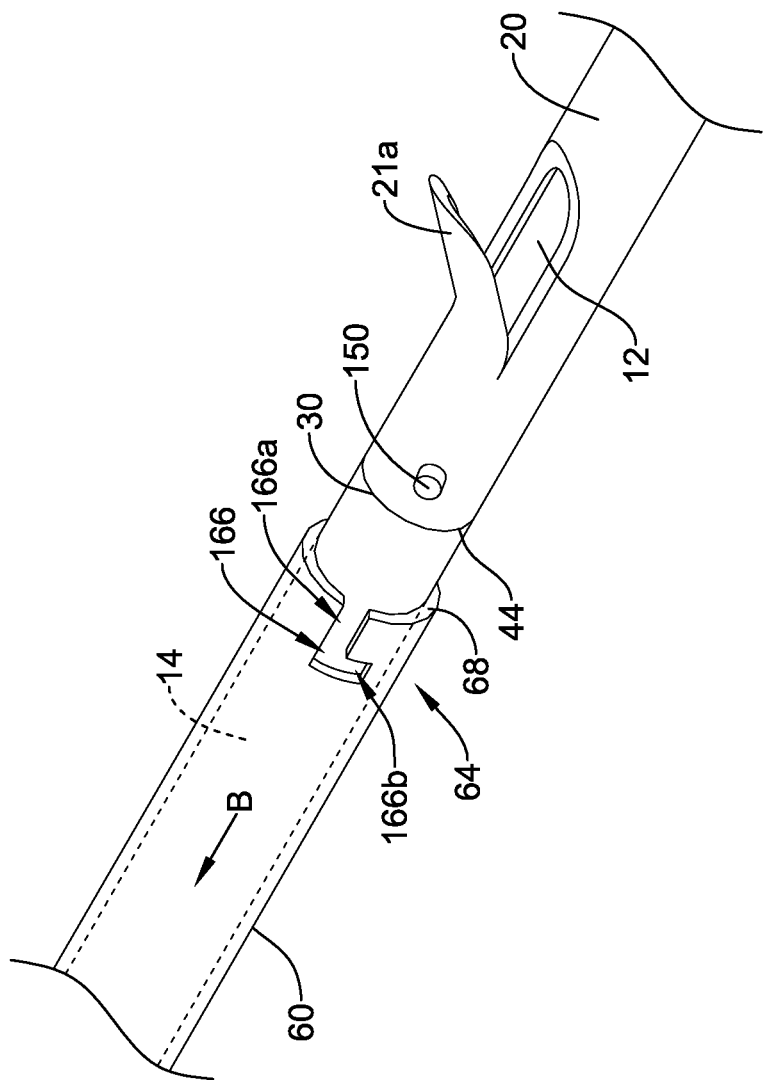

As shown in FIG. 4B at arrow A, in order to decouple the drainage stent 20 from the drainage stent delivery system 10, the outer sheath 60 may be rotated relative to the drainage stent 20 to move the protrusion 150 along the second portion 166*b* to a location that intersects the first portion 166*a* of the slot 166 in the distal portion 64 of the outer sheath 60. Once the protrusion 150 is located at the intersection of the first portion 166*a* and the second portion 166*b* of the slot 166, the outer sheath 60 may be translated longitudinally relative to the drainage stent 20 in a proximal direction, shown by arrow B of FIG. 4C, to a second or disengaged position to withdraw the protrusion 150 from the slot 66. Thus, subsequent to rotating the distal portion 64 of the outer sheath 60, the outer sheath 60 may be withdrawn proximally (e.g., translated longitudinally) to a second position such that the distal end 68 of the outer sheath 60 is proximal of the proximal end 44 of the drainage stent 20. Accordingly, in a first rotational orientation, shown in FIG. 4A, the protrusion 150 is not releasable from the slot 166 through longitudinal actuation of the outer sheath 60, and in a second rotational orientation, shown in FIG. 4B, the protrusion 150 is releasable from the slot 166 through longitudinal actuation of the outer sheath 60. Moreover, in the first rotational orientation, the outer sheath 60 is not longitudinally actuatable or translatable from the first position to the second position, but in the second rotational orientation, the outer sheath 60 is longitudinally actuatable or translatable from the first position to the second position. Thus, in at least some instances actuating the outer sheath 60 from the first position to the second position requires rotating the distal portion 64 of the outer sheath 60 relative to the drainage stent 20 to permit longitudinal actuation or translation of the outer sheath 60 from the first position to the second position.

Figure 4D:
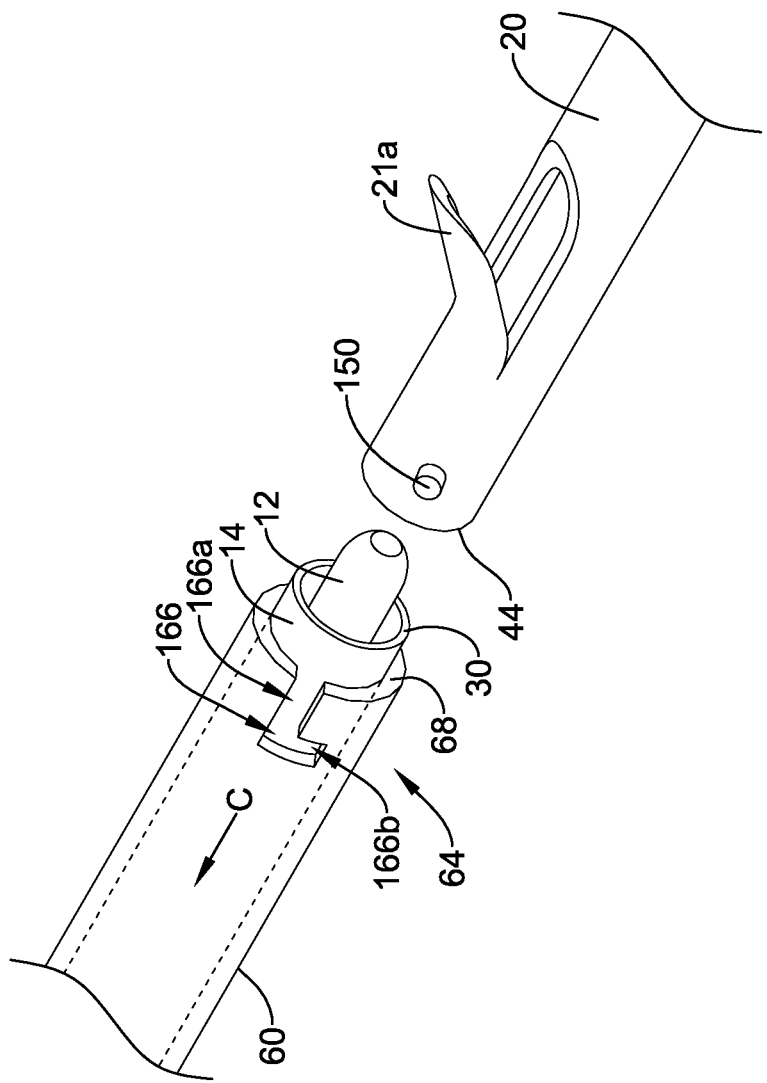

As shown by arrow C in FIG. 4D, with the protrusion 150 removed from the slot 166, the push catheter 14 and guide catheter 12, along with the outer sheath 60, may be withdrawn proximally while the drainage stent 20 is maintained at the target location in a body lumen. The push catheter 14, guide catheter 12 and the outer sheath 60 may be withdrawn proximally in any desired order. For example, in some instances, the guide catheter 12 may be withdrawn first, leaving the push catheter 14 in position with the distal end 30 of the push catheter facing and/or abutting the proximal end 44 of the drainage stent 20 to hold the drainage stent 20 stationary while the guide catheter 12 is withdrawn from the lumen of the drainage stent 20. Subsequently, the push catheter 14, the guide catheter 12, and the outer sheath 60, may be withdrawn from the patient. In other instances, the push catheter 14, the guide catheter 12, and/or the outer sheath 60, may be withdrawn simultaneously or sequentially in another desired order.

In some embodiments, the slot 166 may only extend through a portion of the thickness of the tubular wall of the outer sheath 60, thus defining a groove in the tubular wall of the outer sheath 60. The protrusion 150 could be configured to engage in this groove, which would be located in a surface of the outer sheath 60. In some embodiments, the protrusion 150 and slot 166 (which may be a groove in some instances) may be designed to form an interference fit, permitting further control of the drainage stent 20 prior to deployment of the drainage stent 20. For example, in some embodiments the protrusion 150 and the slot 166 may fit together as a wedge or by elastic deformation of one or both of the engaging features.

In instances in which it is desired to reposition and/or retrieve the drainage stent 20, the process of decoupling the outer sheath 60 from the drainage stent 20 may be reversed. For example, the outer sheath 60 may be advanced distally such that the protrusion 150 passes into the first portion 66*a* of the slot 66. The outer sheath 60 may then be rotated relative to the drainage stent 20 to position the protrusion 150 in the second portion 66*b* of the slot 66 to couple the drainage stent 20 to the outer sheath 60. With the drainage stent 20 coupled to the outer sheath 60, the outer sheath 60 may be actuated (advanced/withdrawn) to reposition and/or retrieve the drainage stent 20.

FIGS. 5A-5D illustrate the functionality of another exemplary retention structure for selectively retaining the drainage stent 20 to the drainage stent delivery system 10. Although the outer sheath 60 of the drainage stent delivery system 10 is illustrated as being selectively surrounding a portion of the drainage stent 20, it is understood that in some embodiments another elongate shaft of the drainage stent delivery system 10 may selectively surround a portion of the drainage stent 20, in the manner described with regard to FIGS. 5A-5D.

Figure 5A:
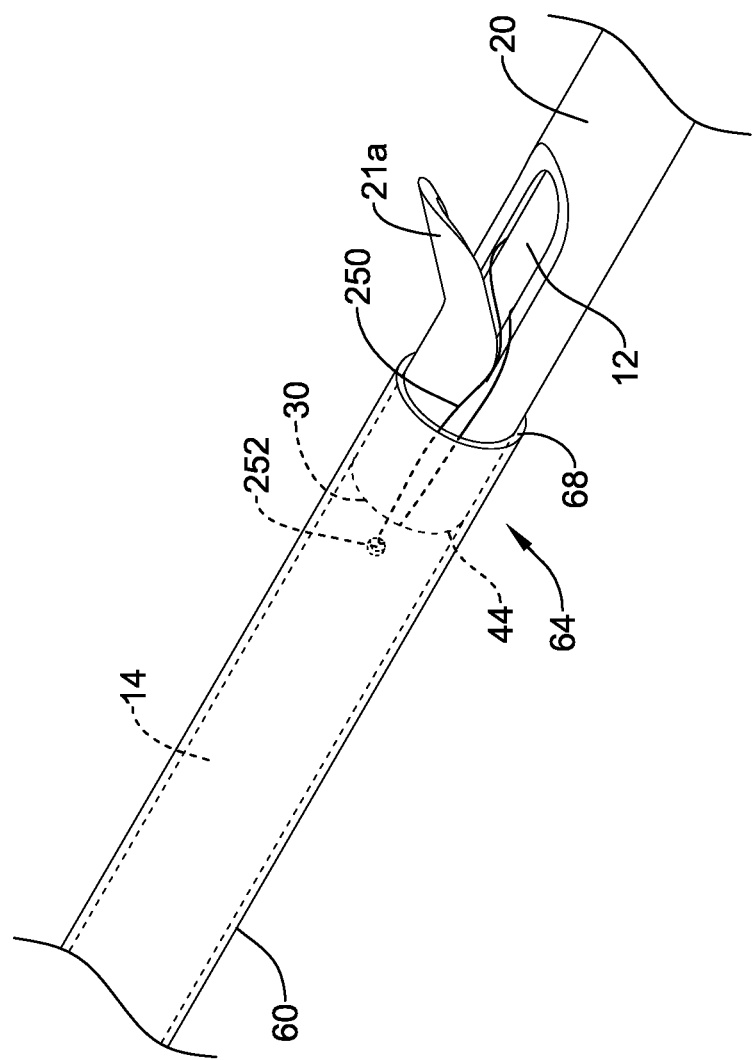
FIGS. 5A-5D are perspective views illustrating the functionality of another retention structure for selectively retaining a stent to an elongate shaft of a delivery system.

As shown in FIG. 5A, the outer sheath 60 may extend distally over at least a portion of the drainage stent 20 to facilitate coupling the drainage stent 20 to the drainage stent delivery system 10. For instance, the distal portion 64 of the outer sheath 60 may be configured to receive a proximal portion of the drainage stent 20 therein such that the distal portion 64 of the outer sheath 60 surrounds the proximal portion of the drainage stent 20. It is noted that the distal portion 64 of the outer sheath 60 may extend over the drainage stent 20 for any desired length such that the proximal end 44 of the drainage stent 20 is positioned proximal of the distal end 68 of the outer sheath 60. In some instances, the distal end 68 of the outer sheath 60 may be located proximal of the proximal barb 21*a* of the drainage stent 20, or the distal end 68 of the outer sheath 60 may be located distal of the proximal barb 21*a*. In instances in which the distal end 68 of the outer sheath 60 is positioned distal of the proximal barb 21*a*, the proximal barb 21*a* may be deflected radially inward from an equilibrium position to be disposed in the lumen of the outer sheath 60. In some instances, the distal end 68 of the outer sheath 60 may be positioned distal of the distal barb 21*b*, such that both the proximal barb 21*a* and the distal barb 21*b* are deflected radially inward to be positioned within the lumen of the outer sheath 60. In such instances, the radially deflected barb(s) 21*a*, 21*b* may frictionally engage the inner surface of the outer sheath 60 to facilitate retaining the drainage stent 20. In some instances in which the distal end 68 of the outer sheath 60 is positioned either proximal or distal of the proximal barb 21*a*, the lumen of the outer sheath 60 may be sized to frictionally engage the outer surface of the tubular wall of the drainage stent 20 to facilitate retaining the drainage stent 20 to the outer sheath 60.

When disposed in the distal portion 64 of the outer sheath 60, the proximal end 44 of the drainage stent 20 may face and/or abut the distal end 30 of the push catheter 14, which extends through the lumen of the outer sheath 60, while the guide catheter 12 extends through the lumen 28 of the push catheter 14 and the lumen of the drainage stent 20.

FIG. 5A illustrates the outer sheath 60 in a first or engaged position in which the drainage stent 20 is coupled to the drainage stent delivery system 10. In the engaged position, the distal portion 64 of the outer sheath 60 may surround at least a proximal portion of the drainage stent 20. For example, as shown in FIG. 5A, in the first position, the distal portion 64 of the outer sheath 60 may surround the proximal portion of the drainage stent 20 such that the proximal barb 21*a* is located distal of the distal end 68 of the outer sheath 60.

In addition to the outer sheath 60, the drainage stent delivery system 10 may include means for releasably connecting the drainage stent 20 to the push catheter 14. Some suitable means are disclosed in U.S. Pat. Nos. 5,921,952 and 6,562,024, the disclosures of which are incorporated herein by reference. For example, a suture 250, attached to the push catheter 14, may be used to releasably connect the drainage stent 20 to the push catheter 14. The suture 250 may extend through an opening 252 in the tubular wall of the push catheter 14, forming a loop. The loop portion of the suture 250 may be passed through an opening, such as the opening formed through the tubular wall of the drainage stent 20 consequent the formation of the proximal barb 21a or a separate opening, into the lumen of the drainage stent 20. The loop portion of the suture 250 may extend around a portion of the guide catheter 12 within the lumen of the drainage stent 20. As will be further described herein, as the guide catheter 12 is moved longitudinally in a proximal direction relative to the drainage stent 20 and the push catheter 14, the suture 250 may be freed from the guide catheter 12, and thus releasing the drainage stent 20 from the push catheter 14.

In some instances, the lumen of the outer sheath 60 may be sized to closely retain the suture 250 against the outer surface of the drainage stent 20 to help retain the suture 250 in position in order to reduce the risk of premature deployment of the drainage stent 20. Thus, in some instances, a portion of the suture 250 extending from the opening 252 may be positioned between the inner surface of the outer sheath 60 and the outer surface of the drainage stent 20.

Figure 5B:
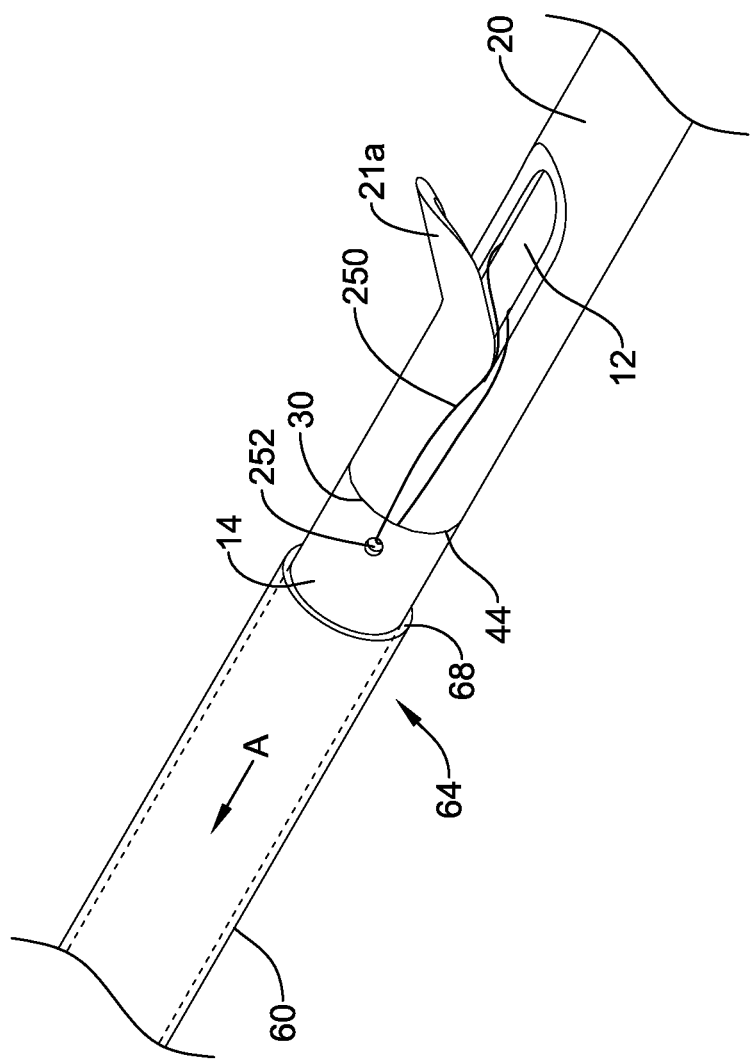

As shown in FIG. 5B at arrow A, in order to decouple the drainage stent 20 from the drainage stent delivery system 10, the outer sheath 60 may be translated longitudinally relative to the drainage stent 20 in a proximal direction to a second or disengaged position such that the distal end 68 of the outer sheath 60 is proximal of the proximal end 44 of the drainage stent 20. Proximal actuation of the outer sheath 60 may free the suture 250 from constraint between the inner surface of the outer sheath 60 and the outer surface of the drainage stent 20.

Figure 5C:
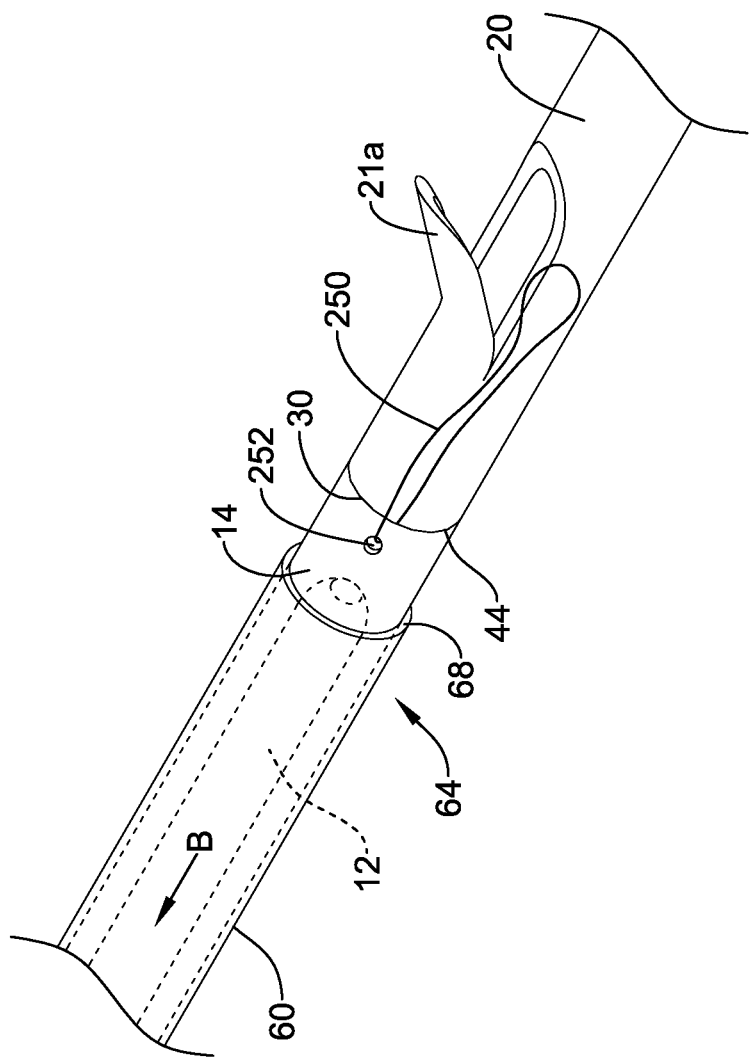
Figure 5D:
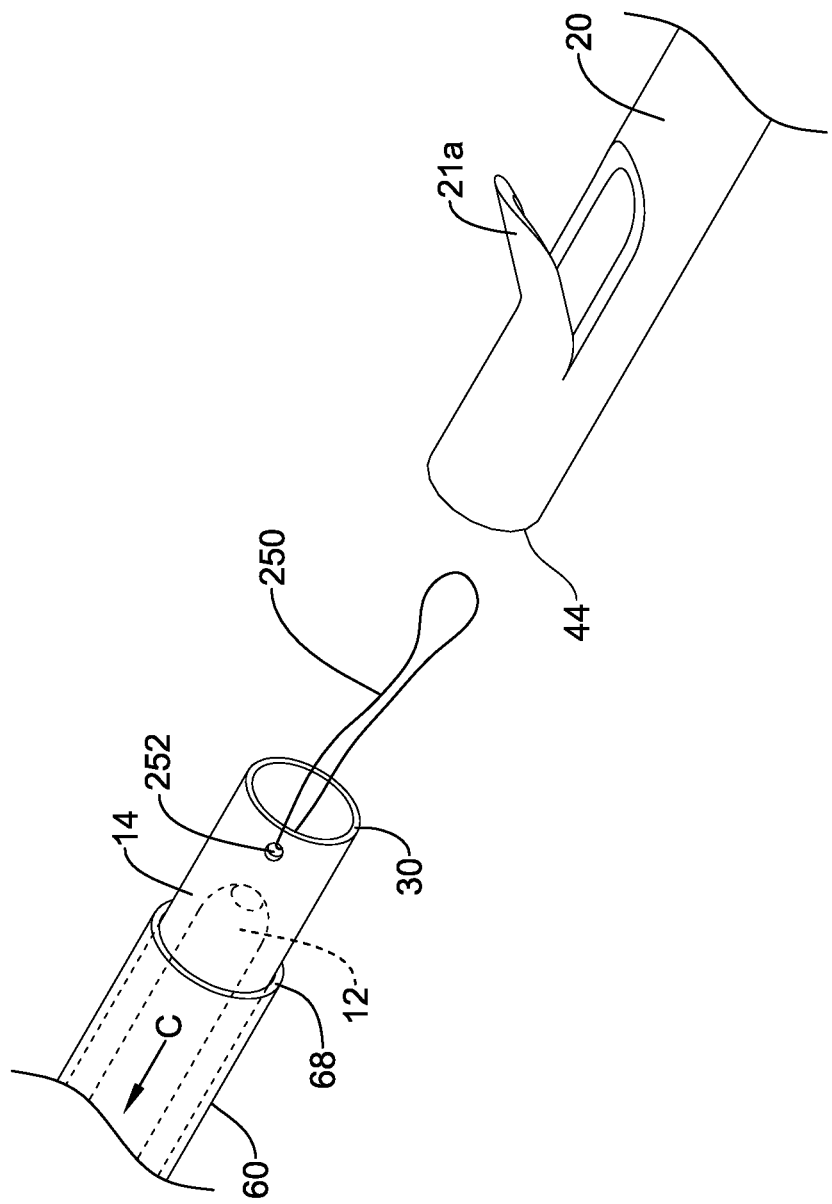

With the drainage stent 20 positioned at the target location in a lumen, the operator may then withdraw the guide catheter 12 proximally relative to the push catheter 14 and the drainage stent 20, as shown in FIG. 5C at arrow B. For instance, the operator may grasp the knob 42 with one hand and grab the handle assembly 16 with another hand, then pull the knob 42 proximally away from the handle assembly 16 to withdraw the guide catheter 12. It is noted that the handle assembly 16 may have other configurations, such as a trigger grip or other conventional configuration, which may be manipulated to withdraw the guide catheter 12 from the drainage stent 20 or otherwise actuate deployment of the drainage stent 20.

Once the drainage stent 20 is disengaged from the outer sheath 60, withdrawing the guide catheter 12 proximally while the proximal end 44 of the drainage stent 20 abuts the distal end 30 of the push catheter 14, holding the drainage stent 20 stationary relative to the push catheter 14, may release the drainage stent 20 from the drainage stent delivery system 10 in order to deploy the drainage stent 20 at the target location. For instance, proximal longitudinal movement of the guide catheter 12 such that the distal end of the guide catheter 12 is proximal of the distal end of the push catheter 14 will release the suture 250 from the opening of the drainage stent 20, and thus release the drainage stent 20 from the push catheter 14 for deployment in the lumen.

Once the drainage stent 20 has been properly deployed at the target location, the drainage stent delivery system 10 may then be withdrawn. For instance, as shown by arrow C in FIG. 5D, with the suture 250 released from the guide catheter 12 and the drainage stent 20, the push catheter 14 and guide catheter 12, along with the outer sheath 60, may be withdrawn proximally while the drainage stent 20 is maintained at the target location in a body lumen. The push catheter 14, guide catheter 12 and the outer sheath 60 may be withdrawn proximally in any desired order. For example, in some instances, the push catheter 14, the guide catheter 12, and/or the outer sheath 60, may be withdrawn simultaneously or sequentially, as desired.

In instances in which it is desired to reposition and/or retrieve the drainage stent 20, the process of decoupling the outer sheath 60 from the drainage stent 20 may be reversed. For example, the outer sheath 60 may be advanced distally over a proximal portion of the drainage stent 20. With the drainage stent 20 coupled to the outer sheath 60, the outer sheath 60 may be actuated (advanced/withdrawn) to reposition and/or retrieve the drainage stent 20.

It is noted that although several examples of an engaging feature of the drainage stent 20 which engages with an engaging feature of the outer sheath 60 to selectively couple the drainage stent 20 to the outer sheath 60 are illustrated herein, in other embodiments the engaging feature of the drainage stent 20 and the engaging feature of the outer sheath 60 may be reversed, such that the drainage stent 20 includes an opening (e.g., slot or groove) or other engaging feature that receives a protrusion, tab or other engaging feature of the outer sheath 60. For example, FIG. 6 illustrates another exemplary retention structure for selectively retaining the drainage stent 20 to the drainage stent delivery system 10.

Figure 6:
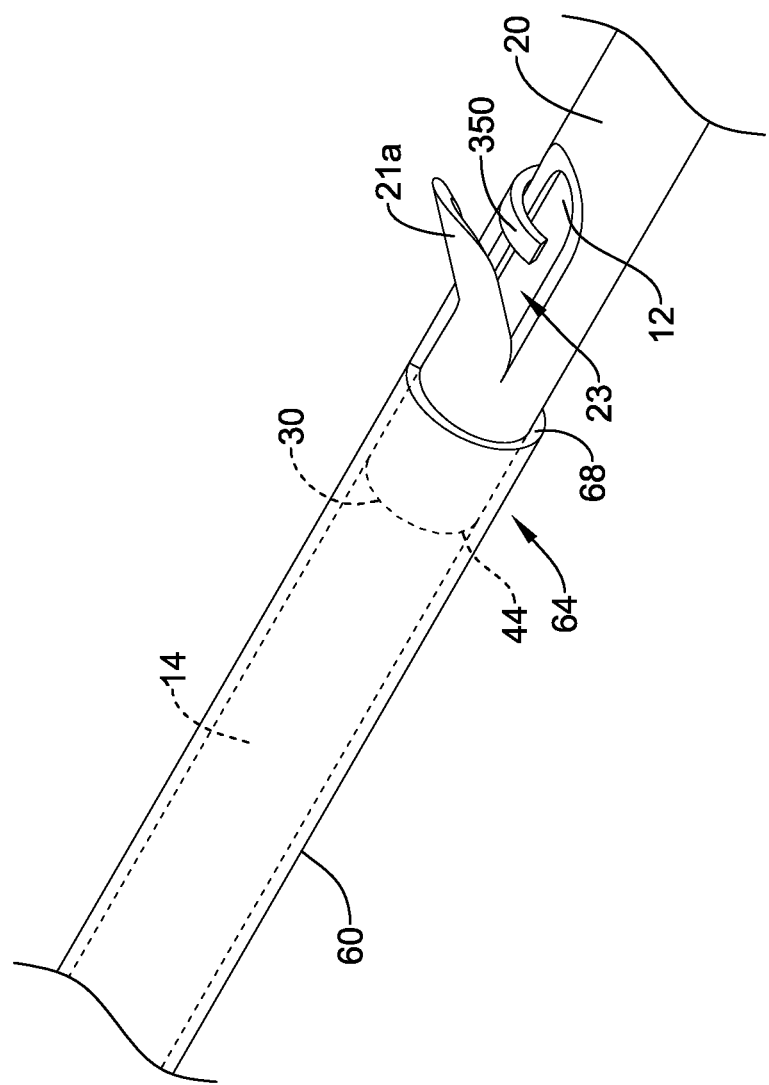
FIG. 6 is a perspective view illustrating another retention structure for selectively retaining a stent to an elongate shaft of a delivery system.

As shown in FIG. 6, the outer sheath 60 may extend distally over at least a portion of the drainage stent 20 to facilitate coupling the drainage stent 20 to the drainage stent delivery system 10. For instance, the distal portion 64 of the outer sheath 60 may be configured to receive a proximal portion of the drainage stent 20 therein such that the distal portion 64 of the outer sheath 60 surrounds the proximal portion of the drainage stent 20. It is noted that the distal portion 64 of the outer sheath 60 may extend over the drainage stent 20 for any desired length such that the proximal end 44 of the drainage stent 20 is positioned proximal of the distal end 68 of the outer sheath 60. In some instances, the distal end 68 of the outer sheath 60 may be located proximal of the proximal barb 21a of the drainage stent 20, or the distal end 68 of the outer sheath 60 may be located distal of the proximal barb 21a. In some instances, the lumen of the outer sheath 60 may be sized to frictionally engage the outer surface of the tubular wall of the drainage stent 20 to facilitate retaining the drainage stent 20 to the outer sheath 60.

When disposed in the distal portion 64 of the outer sheath 60, the proximal end 44 of the drainage stent 20 may face and/or abut the distal end 30 of the push catheter 14, which extends through the lumen of the outer sheath 60, while the guide catheter 12 extends through the lumen 28 of the push catheter 14 and the lumen of the drainage stent 20.

The outer sheath 60 may include a tab 350, such as a flap or protuberance, for engaging a portion of the drainage stent 20, such as an opening (e.g., slot, groove, hole). In some instances, the tab 350 may extend from the outer sheath 60, such as from the distal end 68 of the outer sheath 60, or be formed of a portion of the tubular wall of the outer sheath 60. In some instances, the tab 350 may engage or be received in the opening 23 of the drainage stent 20 formed consequent the formation of the proximal tab 21a from the tubular wall of the drainage stent 20 and/or the tab 350 may be positioned distal of the proximal tab 21a and be engaged with the proximal tab 21a. Alternatively, the tab 350 may interact with the distal tab 21b and associated opening of the drainage stent 20. In other embodiments, the drainage stent 20 may include a discrete opening (e.g., slot, groove, hole) formed therein either proximal or distal of the barb 21a for receiving the tab 350 of the outer sheath 60.

In order to release the drainage stent 20 from the outer sheath 60, and thus deploy the drainage stent 20, the outer sheath 60 may be rotated relative to the drainage stent 20 to move the tab 350 out of the opening 23 and/or out of engagement with the barb 21a (or other engagement feature of the drainage stent 20. Once the tab 350 is disengaged from the engagement feature of the drainage stent 20, the outer sheath 60 may be translated longitudinally relative to the drainage stent 20 in a proximal direction to a second or disengaged position in which the distal end 68 of the outer sheath 60 is proximal of the proximal end 44 of the drainage stent 20 and the tab 350 is proximal of the opening 23 and barb 21a or other opening or engagement feature of the drainage stent 20. Alternatively, the tab 350 may be sufficiently deflectable such that the outer sheath 60 may be translated longitudinally relative to the drainage stent 20 in a proximal direction without rotation of the outer sheath 60, which will deflect the tab 350 until the tab 350 becomes disengaged from the engagement feature of the drainage stent 20 and allows the drainage stent 20 be become decoupled from the outer sheath 60. In other words, the outer sheath 60 may be pulled proximally, thereby deflecting the tab 350. Once the tab 350 has deflected a sufficient amount to become removed from the opening 23 (or other discrete opening) and/or has deflected a sufficient amount to pass proximally of the barb 21a, the drainage stent 20 may be released from the outer sheath 60.

Accordingly, in some instances, detachment of the drainage stent 20 may be achieved with rotation, however, in other instances, detachment of the drainage stent 20 may be achieved, for example, by longitudinal displacement (e.g., pulling) of the outer sheath 60 (with or without rotation) while holding the drainage stent 20 stationary with the push catheter 14.

Although several illustrated embodiments of the disclosed stent retention structures are illustrated as being incorporated into a delivery system for delivering a drainage stent, it is understood that the stent retention structures may also be used to selectively couple other stent or endoprosthesis devices to a delivery system. For example, in some instances the stent retention structures described herein may be used to selectively couple a vascular stent to an elongate member of a delivery system for delivering the vascular stent to a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent delivery system comprising:
    a stent having a proximal end, a distal end, and a lumen extending therethrough;
    a guide catheter extending through the lumen of the stent;
    a push catheter disposed over a portion of the guide catheter proximal of the distal end of the stent;
    an outer sheath slidably disposed over the push catheter and surrounding at least a portion of the stent, the outer sheath being actuatable from a first position in which a distal portion of the outer sheath surrounds at least a portion of the stent to a second position in which the distal portion of the outer sheath is proximal of the proximal end of the stent; and
    a retention mechanism for selectively coupling the stent to the outer sheath through rotational motion of the outer sheath relative to the stent.

2. The stent delivery system of claim 1, wherein the outer sheath must be rotated relative to the stent to permit actuation of the outer sheath from the first position to the second position.

3. The stent delivery system of claim 2, wherein the retention mechanism includes an engaging feature of the outer sheath which engages a portion of the stent.

4. The stent delivery system of claim 3, wherein the engaging feature is a tab configured to receive the portion of the stent.

5. The stent delivery system of claim 3, wherein the engaging feature is a slot configured to receive the portion of the stent.

6. The stent delivery system of claim 5, wherein the portion of the stent is an outwardly extending barb.

7. The stent delivery system of claim 5, wherein the portion of the stent is a radially extending protrusion.

8. The stent delivery system of claim 5, wherein a distal end of the push catheter is positioned proximal of the proximal end of the stent.

9. The stent delivery system of claim 2, wherein the outer sheath includes a slot extending proximally from a distal end of the outer sheath for receiving a portion of the stent therein; and
    wherein in a first rotational orientation, the portion of the stent is not releasable from the slot through longitudinal actuation of the outer sheath and in a second rotational orientation the portion of the stent is releasable from the slot through longitudinal actuation of the outer sheath.

10. The stent delivery system of claim 2, wherein the outer sheath includes a tab for receiving a portion of the stent; and
    wherein in a first rotational orientation, the portion of the stent is not releasable from the tab through longitudinal actuation of the outer sheath and in a second rotational orientation the portion of the stent is releasable from the tab through longitudinal actuation of the outer sheath.

* * * * *